United States Patent
Naya et al.

(10) Patent No.: US 7,579,588 B2
(45) Date of Patent: Aug. 25, 2009

(54) BASE PLATE FOR USE IN MASS SPECTROMETRY ANALYSIS, AND METHOD AND APPARATUS FOR MASS SPECTROMETRY ANALYSIS

(75) Inventors: Masayuki Naya, Ashigarakami-gun (JP); Hisashi Ohtsuka, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 202 days.

(21) Appl. No.: 11/642,535

(22) Filed: Dec. 21, 2006

(65) Prior Publication Data

US 2007/0158549 A1 Jul. 12, 2007

(30) Foreign Application Priority Data

Dec. 22, 2005 (JP) ............................. 2005-369441

(51) Int. Cl.
*H01J 49/00* (2006.01)
(52) U.S. Cl. ..................................................... 250/288
(58) Field of Classification Search ................. 250/288; 356/301; 436/518; 435/287.2
See application file for complete search history.

(56) References Cited

U.S. PATENT DOCUMENTS

| | | | | |
|---|---|---|---|---|
| 5,017,007 | A * | 5/1991 | Milne et al. | 356/301 |
| 5,955,729 | A | 9/1999 | Nelson et al. | |
| 6,475,808 | B1 * | 11/2002 | Wagner et al. | 506/18 |
| 6,569,383 | B1 | 5/2003 | Nelson et al. | |
| 6,838,297 | B2 | 1/2005 | Iwasaki et al. | |
| 7,247,469 | B2 * | 7/2007 | Wagner et al. | 435/287.2 |
| 2004/0183176 | A1 | 9/2004 | Naya et al. | |
| 2005/0059086 | A1 | 3/2005 | Huang et al. | |
| 2005/0105085 | A1 | 5/2005 | Naya | |
| 2006/0001872 | A1 | 1/2006 | Naya | |
| 2007/0030481 | A1 | 2/2007 | Gilbert | |

FOREIGN PATENT DOCUMENTS

| | | |
|---|---|---|
| EP | 0 984 269 A1 | 3/2000 |
| JP | 9-320515 A | 12/1997 |
| WO | WO 97/09608 A1 | 3/1997 |
| WO | 03064594 A3 | 8/2003 |
| WO | 2004008120 A1 | 1/2004 |

OTHER PUBLICATIONS

Yao J L et al: A Complementary Study of Surface-Enhanced Raman Scattering and Metal Nanorod Arrays, Pure & Applied Chemistry, Pergamon Press, Oxford, GB, vol. 72, No. 1, 2000, pp. 221-228, XP001205200.

(Continued)

*Primary Examiner*—Kiet T Nguyen
(74) *Attorney, Agent, or Firm*—Sughrue Mion, PLLC (57) ABSTRACT

A base plate for mass spectrometry analysis is disclosed, which is used in a method in which a substance immobilized on a surface of the base plate is desorbed from the surface by application of laser light thereto and the ion of the desorbed substance is captured for mass spectrometry analysis. The base plate includes, on at least a portion of the surface thereof, a roughened metal surface capable of exciting local plasmon when exposed to laser light. The roughened metal surface is formed, for example, by forming numerous micropores in a surface of an alumina layer and filling gold particles in the micropores. Each gold particle has a head portion having a size larger than a diameter of the micropore and projecting from the surface of the alumina layer. Use of this base plate allows use of lower-power laser light.

8 Claims, 3 Drawing Sheets

OTHER PUBLICATIONS

Felidj N et al: Optimized surface-enhanced Raman scattering on gold nanoparticle arrays, Applied Physics Letters, American Institute of Physics. New York, US, vol. 82, No. 18, May 5, 2003, pp. 3095-6951.

Vo-Dinh T: "Surface-enhanced Raman spectroscopy using metallic nanostructures", Trac, Trends in Analytical Chemistry, Analytical Chemistry. Cambridge, GB, vol. 17, No. 8-9, Aug. 9, 1998, pp. 557-582.

* cited by examiner

BASE PLATE FOR USE IN MASS SPECTROMETRY ANALYSIS, AND METHOD AND APPARATUS FOR MASS SPECTROMETRY ANALYSIS

BACKGROUND OF THE INVENTION

1. Field of the Invention

The present invention relates to an apparatus and a method for mass spectrometry analysis, in which a substance immobilized on a surface of a base plate is exposed to laser light and is desorbed from the surface, and the desorbed substance is captured to be analyzed. The present invention further relates to a base plate for mass spectrometry analysis, which is used in such apparatuses and methods.

2. Description of the Related Art

As a conventional method for detecting the presence and the like of a specific substance in a sample, Raman spectroscopy is known, and a description of the Raman spectroscopy is found, for example, in U.S. Patent Application Publication No. 20060001872. The method described in this document uses a dielectric base plate that has metal particles distributed on a surface thereof. The sample is contacted with the surface of the base plate, and then the surface is exposed to laser light to generate Raman scattered light. The thus generated Raman scattered light is subjected to spectroscopic detection. Based on the detected spectrum, whether the specific substance is adhering on the base plate surface is determined, and further, the molecular structure or the like of the substance is analyzed. Using the dielectric base plate having metal particles distributed on the surface thereof in this method, local plasmon is excited at a portion of the metal particles exposed to the laser light, and the Raman scattered light is significantly enhanced by the local plasmon resonance to allow highly accurate analysis.

It should be noted that, besides using the dielectric base plate having metal particles distributed on the surface thereof, as described above, the similar Raman scattered light enhancing effect utilizing the local plasmon resonance can be obtained by using a base plate including a metal surface having a micro-pattern including numerous convex and concave portions fabricated thereon, or a base plate describes in U.S. Patent Application Publication No. 20050105085, which has numerous micropores formed in the surface of a dielectric body thereof and metal particles filled in the micropores such that head portions of the metal particles, each having a size larger than a diameter of the micropores, project from the dielectric surface.

On the other hand, as a conventional apparatus for performing mass spectrometry analysis of a substance, a Time of Flight Mass Spectrometer (TOF-MAS), as described, for example, in Japanese Unexamined Patent Publication No. 9(1997)-320515 is known. The TOF-MAS carries out mass spectrometry analysis of a substance based on a time of flight that is acquired by exposing the substance immobilized on the surface of the base plate to laser light or the like to desorb the substance from the surface, and detecting a time taken by the ion of the desorbed substance to fly a predetermined distance.

It is likely that, after the presence of a specific substance in a certain sample is detected by using the above-described Raman spectroscopy, the mass of the substance is analyzed by using, for example, the above-described TOF-MAS. In such a case, it is naturally necessary to perform mass spectrometry analysis without mistaking the substance whose presence has been detected for another substance. It should be noted that International Patent Publication No. WO97/009608 has proposed a mass spectrometry analysis method in which the same base plate is used for substance detection according to Raman spectroscopy utilizing surface plasmon resonance and for mass spectrometry analysis using a TOF-MAS.

According to the mass spectrometry analysis method disclosed in International Patent Publication No. WO97/009608, a specific substance, whose presence in a sample has been confirmed using Raman spectroscopy, can reliably be subjected to mass spectrometry analysis without mistaking the substance for another substance. However, this method has a drawback in that high-power laser light is necessary to ionize the substance immobilized on the surface of the base plate to desorb the substance from the surface.

SUMMARY OF THE INVENTION

In view of the foregoing circumstances, the present invention is directed to enable use of laser light of lower power than those used in prior art methods and apparatuses where a substance immobilized on the surface of the base plate is exposed to laser light to be desorbed from the surface, and ions of the desorbed substance are captured for mass spectrometry analysis.

The present invention is further directed to provide a base plate for use in mass spectrometry analysis, which allows use of lower power laser light as described above.

A first aspect of the base plate for mass spectrometry analysis according to the invention is a base plate for use in a method in which a substance immobilized on a surface of the base plate is desorbed from the surface by application of laser light thereto and the desorbed substance is captured for mass spectrometry analysis, as described above, and the base plate includes, on at least a portion of the surface thereof, a roughened metal surface capable of exciting local plasmon when exposed to laser light.

A second aspect of the base plate for mass spectrometry analysis according to the invention is a base plate for use in a method in which an ionized substance immobilized on a surface of the base plate is desorbed from the surface by application of laser light thereto and the desorbed ionized substance is captured for mass spectrometry analysis, and the base plate includes, on at least a portion of the surface thereof, a roughened metal surface capable of exciting local plasmon when exposed to laser light.

A third aspect of the base plate for mass spectrometry analysis according to the invention is a base plate for use in a method in which a substance immobilized on a surface of the base plate is ionized and desorbed from the surface by application of laser light thereto and the desorbed ionized substance is captured for mass spectrometry analysis, and the base plate includes, on at least a portion of the surface thereof, a roughened metal surface capable of exciting local plasmon when exposed to laser light.

It should be noted that the above-described roughened metal surface may be, for example: a roughened metal surface having a micro-pattern including numerous convex and concave portions fabricated thereon; a roughened metal surface having numerous metal particles fixed on a surface of a dielectric material; or a roughened metal surface including numerous micropores formed in a surface of a dielectric material and metal particles filled in the micropores, in which the metal particles have head portions having a size larger than a diameter of the micropores and projecting from the surface of the dielectric material.

It is desirable that the base plate further includes on the roughened metal surface at least one layer serving to bind the substance to the roughened metal surface. It is further desirable that the roughened metal surface or the surface of the base plate parallel with the roughened metal surface includes on a portion thereof a positioning mark.

A first aspect of the analysis method according to the invention is an analysis method using the above-described base plate for mass spectrometry analysis of the invention, and the method includes: making a substance to be analyzed adhere to the roughened metal surface of the base plate; ionizing the substance to be analyzed; applying laser light to the roughened metal surface to desorb ions of the substance to be analyzed from the roughened metal surface; and capturing the desorbed ion to perform mass spectrometry analysis.

A second aspect of the analysis method according to the invention is an analysis method using the above-described base plate for mass spectrometry analysis of the invention, and the method includes: making a substance to be analyzed adhere to the roughened metal surface of the base plate; applying laser light to the roughened metal surface to ionize the substance to be analyzed; and capturing the ion thus desorbed from the roughened metal surface to perform mass spectrometry analysis.

The above-described mass spectrometry analysis is preferably performed using, for example, a TOF-MAS.

A third aspect of the analysis method according to the invention is an analysis method using the base plate for mass spectrometry analysis of the invention, and the method includes: contacting a sample with the roughened metal surface of the base plate; applying laser light to an area of the roughened metal surface having the sample contacting therewith to excite local plasmon; detecting the presence of a substance to be analyzed in the sample by utilizing the excitation of local plasmon; ionizing the substance; applying laser light to the area of the roughened metal surface having been exposed to the laser light for exciting local plasmon to desorb the ionized substance from the roughened metal surface; and capturing the desorbed ionized substance to perform mass spectrometry analysis.

It is desirable that the presence of the substance to be analyzed in the sample is detected using Raman spectroscopy.

In the third aspect of the analysis method of the invention, it is desirable that the base plate having the above-described positioning mark is used, and the area having been exposed to the laser light for exciting local plasmon is brought into a position, with reference to the positioning mark, where the area is exposed to the laser light for desorbing the substance.

A first aspect of the analysis apparatus according to the invention is an analysis apparatus using the above-described base plate for mass spectrometry analysis of the invention, and the apparatus includes: a laser light applying means for applying laser light to the roughened metal surface of the base plate having a substance to be analyzed adhering thereto to desorb the substance from the roughened metal surface; and an analyzing means for capturing the substance desorbed from the roughened metal surface by the application of laser light and carrying out mass spectrometry analysis.

It is preferred that a TOF-MAS is applied as the above-described analyzing means.

A second aspect of the analysis apparatus according to the invention is an analysis apparatus using the base plate for mass spectrometry analysis of the invention, and the apparatus includes: a first laser light applying means for applying laser light to an area of the roughened metal surface having a sample contacting therewith to excite local plasmon; a detecting means for detecting the presence of a substance to be analyzed in the sample by utilizing the excitation of local plasmon; a second laser light applying means for applying laser light to the area of the roughened metal surface having been exposed to the laser light for exciting local plasmon to desorb the substance from the roughened metal surface; and an analyzing means for capturing the substance desorbed from the roughened metal surface by the application of laser light by the second laser light applying means and carrying out mass spectrometry analysis.

As the above-described detecting means, a detecting means that detects the presence of the substance to be analyzed in the sample using Raman spectroscopy is preferably applicable.

In the second aspect of the analysis apparatus of the invention, it is desirable that the base plate having the above-described positioning mark is used, and the apparatus further includes a positioning means for bringing the area having been exposed to the laser light for exciting local plasmon into a position, with reference to the positioning mark, where the area is exposed to the laser light for desorbing the substance.

The present inventors have found that a substance adhered on a roughened metal surface, which surface is capable of exciting local plasmon when exposed to laser light, can be desorbed from the base plate by exposure to relatively low power laser light. Based on this knowledge, the base plate for mass spectrometry analysis of the invention includes, on at least a portion of the surface thereof, the roughened metal surface capable of exciting local plasmon when exposed to laser light. Therefore, when it is applied to a device such as the TOF-MAS, in which the substance to be analyzed is desorbed by exposure to laser light, ionization of the substance can be achieved with laser light of lower power than those used in conventional devices.

Further, since the above-described base plate is applied to the analysis method and the analysis apparatus of the invention, after the presence of a predetermined substance in a sample is detected by utilizing excitation of local plasmon, the substance to be analyzed can be desorbed from the base plate for mass spectrometry analysis by application of laser light of relatively low power.

Particularly, in the third aspect of the analysis method of the invention and the second aspect of the analysis apparatus of the invention, the detection of the presence of the substance to be analyzed in the sample and the subsequent mass spectrometry analysis of the substance are carried out in a sequential manner. Therefore, a danger of mistaking the sample for another sample, after the detection of the presence of the substance to be analyzed and before the mass spectrometry analysis, can be prevented.

Furthermore, in the third aspect of the analysis method and the second aspect of the analysis apparatus of the invention, particularly when the base plate having the positioning mark is used, so that the area of the base plate exposed to the laser light for exciting local plasmon is brought into a position, with reference to the positioning mark, where the area is exposed to the laser light for ionizing the substance to be analyzed, these two laser exposures can be accurately applied to the same area of the base plate. Therefore, in this case, a danger of mistaking the sample for another sample can naturally be prevented, and in addition, mass spectrometry analysis can be carried out without a danger of mistaking the substance, whose presence has been confirmed based on the local plasmon excitation, for another substance in the same sample.

DESCRIPTION OF THE PREFERRED EMBODIMENTS

Hereinafter, a base plate for mass spectrometry analysis according to one embodiment of the present invention will be described with reference to the drawings.

Figure 1A:
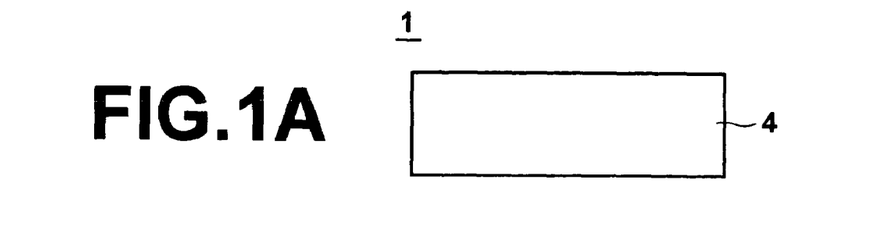
FIGS. 1A to 1C illustrate a production process for a base plate for mass spectrometry analysis according to one embodiment of the present invention.
Figure 1B:
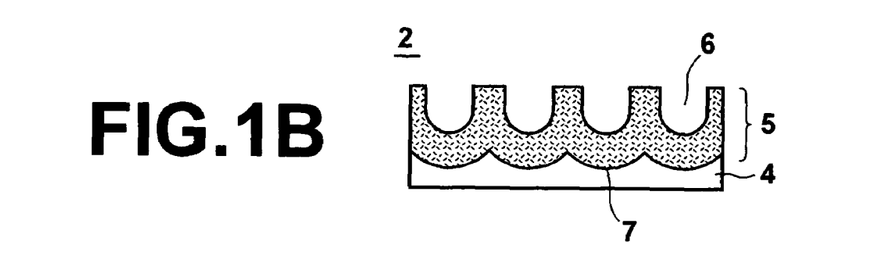
Figure 1C:
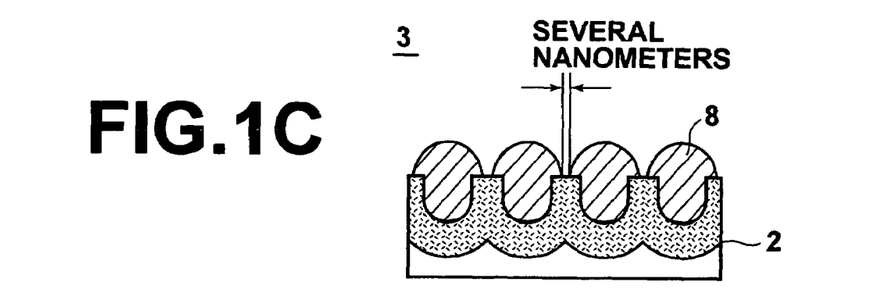

First, a process for producing the base plate for mass spectrometry analysis will be described. The base plate of the invention may be produced using various processes. Among them, a production process using an aluminum substrate will be described herein as an example. FIGS. 1A-1C schematically illustrate sectional shapes of the base plate in various steps of the process in which the base plate of the present embodiment is produced.

FIG. 1A illustrates a substrate 1 before use in the production process for the base plate. In this embodiment, a substrate formed only of an aluminum layer 4 is used as the substrate 1. It should be noted that the substrate 1 may have a structure in which an aluminum or aluminum alloy layer is formed on a support member that is made of a material other than aluminum such as glass. In other words, the structure of the substrate 1 is not particularly limited as long as the surface layer thereof is made of a material whose main component is aluminum.

When producing the base plate for mass spectrometry analysis, first, the surface of the substrate 1 is anodized using an anodizer. For the surface anodization, the substrate 1 fixed in a holder is placed in an electrolyte within a reaction vessel together with a counter electrode. The electrolyte is an acidic electrolyte such as, for example, oxalic acid, phosphoric acid, sulfuric acid or chromic acid. Alternatively, the electrolyte may be a mixture of two or more kinds of acidic solutions.

Next, a voltage is applied between the substrate 1 and the counter electrode. When the voltage is applied, the substrate 1 is connected to the positive side of a power supply, and the counter electrode is connected to the negative side of the power supply. As the voltage is applied, first, an oxide film is formed on the surface of the base plate 1, and then, micro pores are formed on the surface of the oxide film by solvent action of the acid. As the anodization progresses, some of the pores grow preferentially rather than the others, and are arranged at approximately equal intervals. Since a higher electric field is applied on areas of the surface where the pores are formed than other areas thereof, dissolution is promoted, and therefore the pores grow in a direction perpendicular to the surface of the aluminum. On the other hand, areas around the pores remain undissolved. It is one characteristic of the alumina obtained through anodization that the naturally formed micropores are arrayed with very high regularity.

FIG. 1B illustrates a substrate 2 including on a surface thereof an alumina layer 5 having plural micropores 6 formed through the above-described anodization. The micropores 6 are arrayed regularly throughout the almost entire surface of the substrate. The diameter, the depth and the interval of the micropores vary depending on conditions for anodization (such as concentration and temperature of the electrolyte used in anodization, how the voltage is applied, a voltage value, and a time of anodization). Generally, the interval (pitch) between the micropores is in a range from 10 to 500 nm, and the diameter of each micropore is in a range from 5 to 400 nm. The interval and the diameter can respectively be controlled with accuracy. In this embodiment, the conditions for anodization are set so that micropores having a diameter of about 200 nm, a depth of about 100 nm, and an interval of around 300 nm are formed.

It should be noted that Japanese Unexamined Patent Publication Nos. 2001-009800 and 2001-138300 disclose methods for more finely controlling positions and the diameter of formed micropores. By employing these methods, micropores having any diameter, depth and interval can be formed in an array, and a variation in the diameter of the micropores can be controlled to 15% or less.

Next, the micropores 6, which have been naturally formed through the anodization, are filled with gold (Au) through electroplating. When electroplating is carried out, it is necessary to ensure conductivity of micropore bottoms 7. The conductivity of the micropore bottoms 7 can be ensured in various manners such as, for example, controlling the conditions for anodization such that the alumina layer at the micropore bottoms 7 becomes particularly thin, repeating the anodization plural times to thin the alumina layer at the micropore bottoms 7, or etching down the alumina layer at the micropore bottoms 7.

In the electroplating, the substrate 2 is treated in a plating solution. While the alumina layer 5 is nonconductive, conductivity of the micropore bottoms 7 is ensured by the above-described treatment. Therefore, the metal deposits preferentially in the micropores 6 where a stronger electric field is applied, and gold is thus filled in the micropores 6.

In this type of metal particle production process, usually, plating is completed when the metal is filled in the micropores 6. That is, plating is completed when the metal is filled up to the same level as the surface of the substrate 2 or before that. However, in this case, plating is continued after gold is filled to the same level as the surface of the substrate 2. In other words, plating is continued after the micropores 6 have been completely filled with gold until gold is excessively plated around the micropores 6.

That is, what are formed by filling the micropores 6 are only lower portions of gold particles 8, and the gold particles 8 are completed by further forming head portions of the gold particles 8 on the lower portions thereof. Even after the micropores 6 are completely filled with gold, gold deposits around the micropores 6 due to the electric field around the micropores 6. In this manner, the gold particles 8 (having a sort of "mushroom" shape) as shown in FIG. 1C, each having a head portion which projects from the surface of the substrate 2 and has a diameter larger than the diameter of the micropore 6, are formed at the micropores 6.

In this embodiment, plating is continued until a space between each adjacent head portions of the gold particles 8 becomes 10 nm or less. For example, in an experimental stage, plating is conducted while the distance between the head portions of the gold particles 8 is measured with an electron microscope, in order to measure a plating time taken until the distance between the adjacent head portions for most of the gold particles 8 becomes 10 nm or less. Then, in a manufacturing stage, plating can be terminated when the distance between the head portions becomes 10 nm or less by controlling the plating time based on the result of the experiment.

In the above-described process, the metal particles are formed only by plating, and therefore, the base plate for mass spectrometry analysis can be produced relatively easily. Further, the surface structure of the base plate in which the head portions of the gold particles 8 are arrayed with little space therebetween can be obtained. Depending on a formation process for the micropores, the interval between the micropores may not be sufficiently small. However, even in such a case, the space between the head portions of the metal particles can be made small to several nanometers according to this production process.

Figure 2:
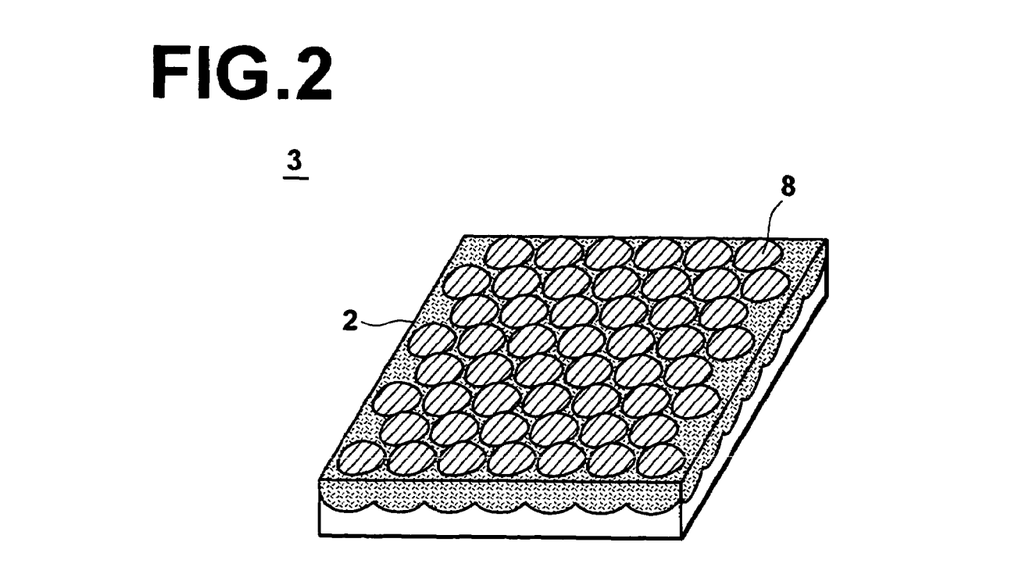
FIG. 2 is a perspective view illustrating a part of the base plate for mass spectrometry analysis.

FIG. 2 is a perspective view illustrating a part of a base plate 3 for mass spectrometry analysis. As shown in FIG. 2, the gold particles 8 are arrayed highly densely throughout the entire surface of the base plate 3. The diameter of the micropores 6 of the base plate 3 is around 200 nm, and the depth thereof is around 100 nm, which is a half of the diameter. The surface of the base plate 3 has a uniform structure, and a variation in the diameter of the micropores 6 is 15% or less. The diameter of the lower portions of the gold particles 8 is slightly smaller than the diameter of the micropores 6, however, is generally around 200 nm. The diameter of the head portions of the gold particles 8 is larger than the diameter of the micropores 6, and a space between each adjacent head portions is several nanometers.

Figure 3:
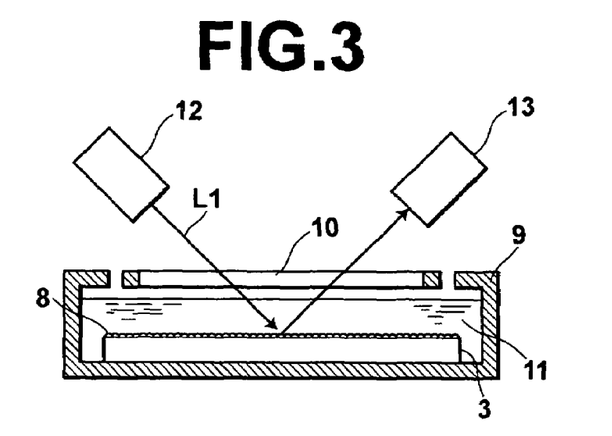
FIG. 3 is a schematic structural diagram illustrating a Raman spectroscopic instrument forming an analysis apparatus according to one embodiment of the invention.

Next, a Raman spectroscopic instrument using the base plate 3 for mass spectrometry analysis that is produced as described above, and analysis using the instrument according to Raman spectroscopy will be described. FIG. 3 illustrates a schematic structure of the Raman spectroscopic instrument. As shown in FIG. 3, this instrument includes a container 9 having a clear window 10, the base plate 3 fixed at a bottom of the container 9, a laser light source 12 serving as a first laser light applying means, which emits laser light toward the base plate 3 in the container 9, and a spectral detector 13 that performs spectroscopy on scattered light on the surface of the base plate 3 to obtain a spectrum of the scattered light, and detects Raman scattered light if it is contained in the scattered light.

The base plate 3 is disposed such that the surface thereof having the above-described projecting head portions of the gold particles 8 faces upward. The container 9 is filled with a liquid sample 11 to be subjected to Raman spectroscopic analysis, and components in the liquid sample 11 can adhere to the surface of the base plate 3.

As laser light L1 is emitted from the light source 12 to the base plate 3 through the clear window 10, the laser light L1 is scattered on the surface of the base plate 3, and the scattered light is detected by the spectral detector 13. The spectral detector 13 performs spectroscopy on the detected scattered light to generate a Raman spectrum. The generated Raman spectrum is outputted to a display screen or a printer which are not shown in the drawings.

Laser light applicable as the laser light L1 in this embodiment is one having a wavelength of, for example, 532 nm, 633 nm or 785 nm. However, the wavelength of the laser light L1 is not limited to these wavelengths, and the wavelength of the laser light L1 is preferably around a wavelength where the plasmon resonance of the base plate 3 is the strongest. Further, the beam diameter of the laser light L1 measured at a position where it is incident on the base plate 3 is set to around 5 μm to 10 μm, and the power thereof is set to around 0.001 mW to 1 mW.

Figure 4:
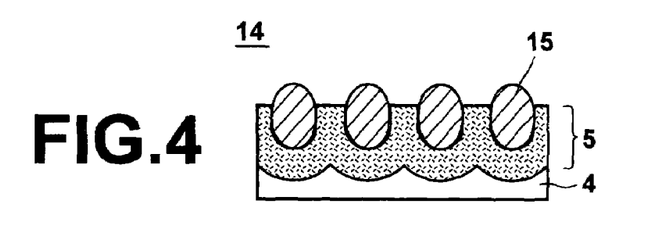
FIG. 4 illustrates a sectional structure of a comparative structure.

In order to confirm advantageous effects of the base plate 3 for mass spectrometry analysis, the present inventors conducted an experiment using a comparative structure 14, as shown in FIG. 4. The comparative structure 14 was produced by forming the alumina layer 5 on the aluminum layer 4 through anodization of the aluminum substrate, and filling the micropores in the alumina layer 5 with gold through electroplating. In this case, plating was terminated before the plated gold exceeded the level of the substrate surface. Subsequent to the plating, the alumina layer 5 was chemically ground to have the head portions of the gold particles 15 project from the substrate surface, as shown in FIG. 4. It should be noted that the diameter, the depth and the interval of the micropores were the same as those of the micropores in the substrate of the base plate 3, and therefore, the size and the shape of lower portions of the gold particles 15 are approximately the same as those of the lower portions of the gold particles 8 of the base plate 3.

Figure 5:
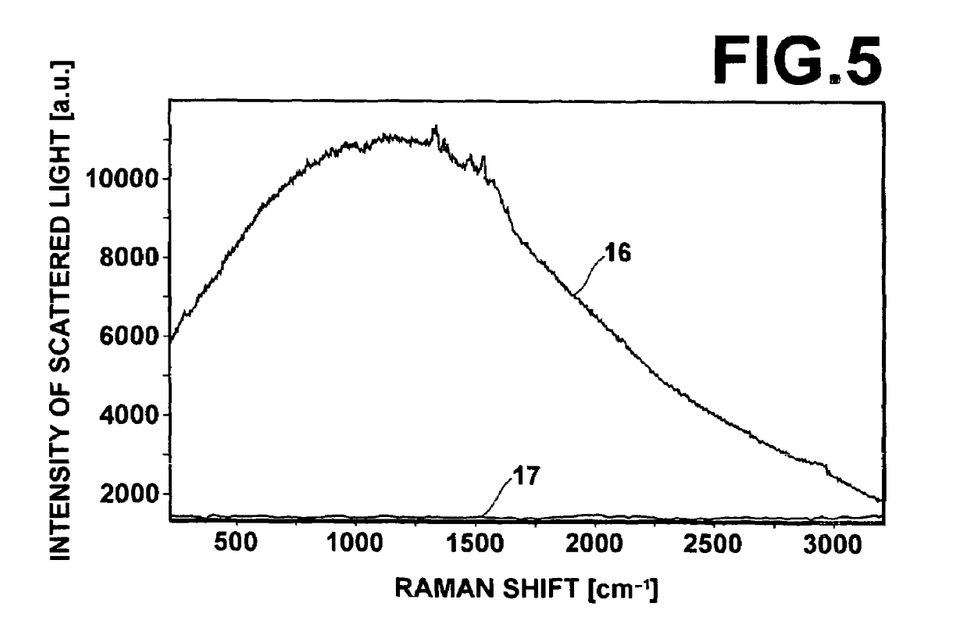
FIG. 5 illustrates an example of Raman spectra.

FIG. 5 illustrates Raman spectra obtained by performing Raman spectroscopy on a methacryl resin (PMMA) using the base plate 3 and the comparative structure 14. The abscissa axis represents a Raman shift ($cm^{-1}$) which is an inverse of a wavelength of light, and the ordinate axis represents an intensity of scattered light (arbitrary unit: a.u.). A spectrum 16 represents a spectrum obtained by Raman spectroscopy using the base plate 3, and a spectrum 17 represents a spectrum obtained by Raman spectroscopy using the comparative structure 14. It can be seen that the Raman spectroscopy using the comparative structure 14 did not provide an effective Raman spectrum. On the other hand, in the Raman spectroscopy using the base plate 3, the Raman scattered light was significantly enhanced and an effective Raman spectrum was obtained.

As described above, the gold particles 8 of the size that is capable of inducing local plasmon resonance are densely distributed throughout the surface of the base plate 3, and the space between the gold particles is relatively small. Therefore, by using the base plate 3 in Raman spectroscopy, Raman scattered light is sufficiently amplified, and accuracy in spectroscopy is improved. Further, since the gold particles 8 are disposed in and on the micropores which has been formed in an array in advance, a uniform structure can be formed throughout the entire surface of the base plate 3, and therefore, approximately the same enhance rate can be obtained throughout the entire surface of the base plate 3.

Furthermore, since the structure of the base plate 3 can be controlled by adjusting the size of the micropores 6 formed in the substrate in advance, the base plates 3 having the same quality can stably be supplied when they are supplied as products. Particularly, by producing the base plate 3 using the combination of anodization and plating as in the present embodiment, the size, shape and interval of the metal particles can be controlled relatively easily, and the base plate for mass spectrometry analysis can be produced at low costs.

By performing Raman spectroscopy using the base plate 3 as described above, Raman scattered light is enhanced to be detected with higher accuracy, and an accurate spectrum can be obtained. This enables accurate detection of a fact that a specific substance is adhering to the base plate 3.

Figure 6:
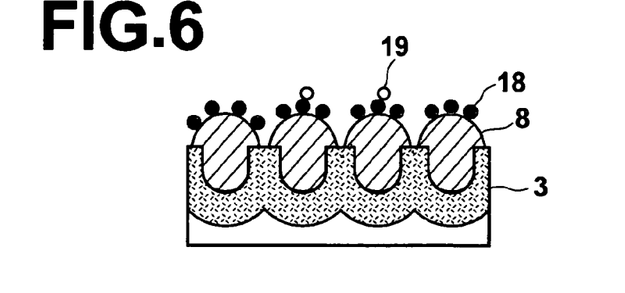
FIG. 6 is a schematic diagram illustrating the base plate for mass spectrometry analysis with a specific substance immobilized on a surface thereof.

It should be noted that a substance which specifically bonds with a test substance subjected to Raman spectroscopy may be immobilized on the gold particles 8 of the base plate 3. As shown in FIG. 6, for example, an antibody substance 18 is immobilized on the gold particles 8, so that when an antigen substance 19, which is a test substance, contacts the surface, a specific chemical bond can be formed between the antigen substance and the antibody substance. In this case, when the specific bond is formed, the spectrum obtained by spectroscopy changes significantly, and this allows highly accurate identification or analysis of molecular structure of the antigen substance. A type of the substance immobilized on the gold particles 8 is appropriately selected depending on the type of the test substance subject to spectroscopy. Such a known combination of the antibody substance 18 and the antigen substance 19 includes, for example, a combination of streptavidin and biotin.

Although the diameter of the head portions of the gold particles 8 is around 200 nm in the present embodiment, the diameter of the head portions of the metal particles is not limited to the above-described embodiment, and may be any size as long as local plasmon resonance can be induced. The local plasmon resonance (the Raman scattered light enhancing effect) occurs when the diameter of the head portions of the metal particles is smaller than the wavelength of light. Therefore, it is preferred that the diameter of the head portions of the metal particles is generally 200 nm or less. However, depending on a wavelength of laser light, local plasmon resonance may be induced even when the diameter of the head portions is somewhat larger than 200 nm.

Further, although the interval between the micropores 6 is around 300 nm in the present embodiment, the interval between the micropores is not limited to this embodiment. However, in order to have the laser light emitted toward the base plate incident on at least one gold particle with certainty, it is advantageous to set the interval between the micropores to be smaller than the beam diameter of the laser light.

It is important to make a space between the adjacent head portions of the metal particles small for improving the Raman scattered light enhancing effect. Therefore, the larger the space between the micropores, the larger diameter of the head portions of the metal particles is necessary. In contrast, if the interval between the micropores is small, a difference between the diameter of the head portions and the diameter of the lower portions of the metal particles may be small.

The metal filled in the micropores 6 through plating, i.e., the material of the metal particles, may be a metal other than gold, such as silver, copper, aluminum, nickel or cobalt, for example. However, since gold has excellent corrosion resistance and is capable of vapor deposition at a relatively low temperature, it can easily be filled in the micropores.

The base plate for mass spectrometry analysis of the invention may also be produced by a process in which micropores are formed in the substrate surface using micromachining technology such as electron beam exposure, nanoimprint or near-field optical lithography, and then the micropores are filled with a metal through plating. In this case, a material forming the substrate needs not be aluminum. For example, a dielectric layer made, for example, of glass or resist may be provided on a conductive layer, and then, micropores, which pass through the dielectric layer to reach the conductive layer, are formed in the dielectric layer using the micromachining technology, and the micropores are filled with a metal through plating.

Figure 7:
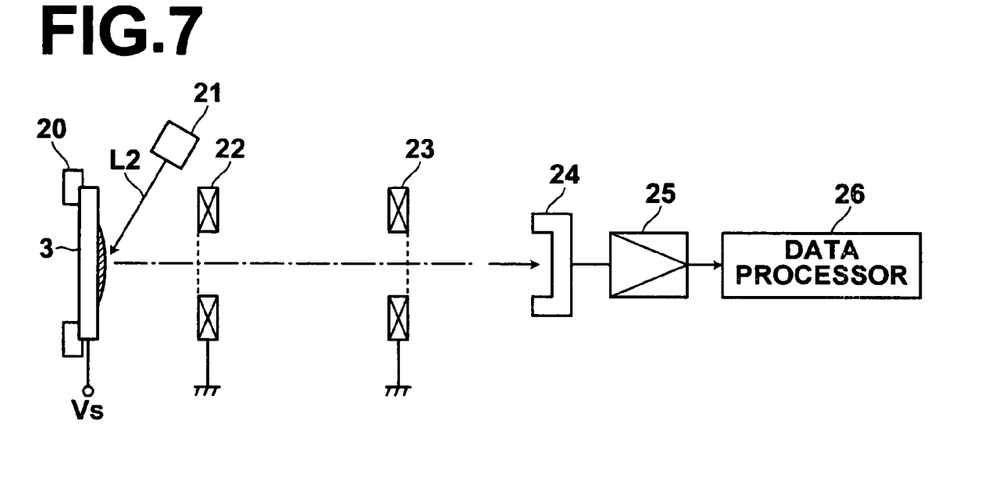
FIG. 7 is a schematic structural diagram illustrating a time of flight mass spectrometer forming the analysis apparatus according to one embodiment of the invention.

Next, a description will be given regarding the application of mass spectrometry analysis to the substance whose presence has been confirmed by the Raman spectroscopy. FIG. 7 illustrates a basic structure of the TOF-MAS (time of flight mass spectrometer), which forms an analysis apparatus according to one embodiment of the invention.

As shown in FIG. 7, this apparatus includes: a base plate holding means 20 for holding the above-described base plate 3 for mass spectrometry analysis; a laser light source 21 that serves as a second laser light applying means for emitting laser light L2 toward a portion of the surface having the gold particles 8 of the base plate 3 held in the base plate holding means 20; an extraction grid 22 disposed to face the surface of the base plate 3; an end plate 23 disposed to face the surface of the base plate 3 via the extraction grid 22; a detector 24 disposed to face the surface of the base plate 3 via the extraction grid 22 and a central hole in the end plate 23; an amplifier 25 for amplifying outputs from the detector 24; and a data processor 26 for processing output signals from the amplifier 25.

Although not shown in the drawing, the whole part of the above structure, or at least the extraction grid 22, the end plate 23 and the detector 24 are placed within a vacuum analysis chamber. In the present embodiment, since the base plate 3 taken out from the Raman spectroscopic instrument have to be carried to this apparatus and to be set in the base plate holding means 20, the base plate holding means 20 and the laser light source 21 are preferably disposed outside the analysis chamber for simplifying a base plate handling mechanism.

Mass spectrometry analysis using the TOF-MAS having the above structure will be described below. Upon mass spectrometry analysis, the base plate 3 is held in the base plate holding means 20, with the surface of the base plate 3 having the gold particles 8 (see FIGS. 1 and 2) facing the laser light source 21 side. A voltage Vs is applied to the base plate 3. In this state, as the laser light source 21 is driven by a predetermined start signal, the laser light source 21 emits the laser light L2 onto the surface of the base plate 3. Laser light applicable as the laser light L2 is, for example, pulse laser light having a wavelength of 337 nm and a pulse duration of about 50 picoseconds to 50 nanoseconds.

The substance present in the liquid sample 11 shown in FIG. 3 is adhering to the surface of the base plate 3. This substance has been ionized in advance, and when it is exposed to the laser light L2, it desorbs from the base plate. The substance thus generated is extracted and accelerated in the direction of the extraction grid 22 due to an electric potential difference Vs between the base plate 3 and the extraction grid 22, and flies to the end plate 23 in a space external to the base plate 3. The velocity of the substance at this time depends on the mass number of the substance. The smaller the mass number, the greater the velocity. This ion passes through the extraction grid 22, flies almost straight within the aforementioned space to pass through the endplate 23, and finally reaches the detector 24.

The output signal from the detector 24 that indicates detection of the ion is amplified to a predetermined level by the amplifier 25, and the amplified signal is inputted to the data processor 26. A synchronization signal for synchronization with the start signal that is supplied to the laser light source 21 is also inputted to the data processor 26. The data processor 26 finds the time of flight based on the synchronization signal and the output signal from the amplifier 25, and then finds the mass number of the substance to be analyzed based on the velocity of the ion derived from the time of flight.

As the base plate on which a substance to be desorbed is immobilized used in the TOF-MAS of the present embodiment, the base plate 3 having the numerous gold particles 8 arrayed on the surface thereof, which is capable of exciting local plasmon when exposed to laser light, is used. Therefore, the substance to be analyzed can be desorbed by the laser light L2 of lower power than those used in convention devices. Specifically, sufficient ionization can be achieved with a laser power of one or more orders of magnitude less than those used in prior art, according to the constitution of the present embodiment.

It should be noted that, although the base plate 3 used in the above-described embodiment has the numerous micropores 6 formed in the surface of the dielectric alumina layer 5 and the micropores 6 filled with the gold particles 8, with the head portions of the gold particles 8 having a size larger than the diameter of the micropores 6 and projecting from the surface of the alumina layer, other type of base plates can also be used. Examples of such base plate include a base plate having a roughened metal surface which is formed by fabricating a micro-pattern including numerous convex and concave portions on a metal surface, and a base plate having a roughened metal surface which is formed by fixing numerous metal particles on a flat dielectric surface. These base plates for mass spectrometry are also capable of exciting local plasmon when exposed to laser light.

Figure 8:
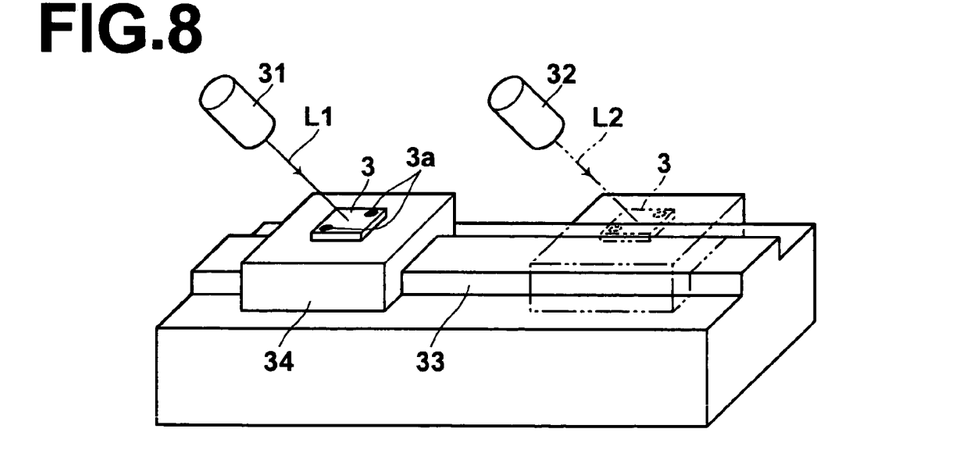
FIG. 8 is a perspective view illustrating a conveyance mechanism for the base plate for mass spectrometry analysis applicable to the analysis apparatus of the invention.

Further, in the analysis apparatus according to the invention, transfer of the base plate may be automated, as shown in FIG. 8, by disposing a first laser light applying means 31, which emits laser light L1 onto the base plate 3 to excite local plasmon, and a second laser light applying means 32, which emits laser light L2 onto the base plate 3 to ionize the substance adhering thereto, in the vicinity of each other, and providing a conveying means 34, which holds and conveys the base plate 3 along, for example, the rail 33 from a position where the base plate is exposed to the laser light L1 to a position where the base plate is exposed to the laser light L2.

In this case, it is desirable to form a positioning mark 3a on the surface of the base plate 3. In a case where the base plate 3 having the positioning mark is used, a photoelectric reading means, for example, reads the positioning mark 3a, and operation of the conveying means 34 is controlled so that the positioning mark 3a read by the reading means is positioned in equal relative positions with respect to the points where the laser light L1 and L2 are applied respectively. In this manner, the portion of the base plate 3 which has been exposed to the laser light L1 can be accurately conveyed to the position where it is exposed to the laser light L2.

Further, on the roughened metal surface formed by the gold particles 8 and the like, at least one layer that serves to bind the substance to be detected to the roughened metal surface may be formed. An example of such a layer is a layer formed by binding peptide on maleimide, shown in Angewandte Chemie International Edition, 2004-43, pp. 5973-5977, FIG. 1-C. The base plate having such a layer bound on the roughened metal surface made, for example, of gold can be used for mass spectrometry analysis using a Matrix Assisted Laser Desorption/Ionization Time of Flight Mass Spectrometer (MALDI-TOF-MAS), for example.

The method used for detecting the presence of a specific substance by exciting local plasmon using the base plate for mass spectrometry analysis of the invention is not limited to the above-described Raman spectroscopy. For example, a method shown in Japanese Unexamined Patent Publication No. 2005-195440, in which the presence of a specific substance is detected by detecting intensity of light that is transmitted or reflected via the roughened metal surface by utilizing the fact that a local plasmon resonance wavelength changes when the specific substance has adhered to the roughened metal surface, is also applicable.

Further, the method used for mass spectrometry analysis using the base plate for mass spectrometry analysis of the invention is not limited to the above-described time of flight mass spectrometry. The base plate for mass spectrometry analysis of the invention is applicable to mass spectrometry methods in general in which laser light is applied to the base plate to desorb the substance to be analyzed.

What is claimed is:

1. An analysis method using a base plate comprising, on at least a portion of the surface thereof, a roughened metal surface capable of exciting local plasmon when exposed to laser light, the method comprising:
    making a substance to be analyzed adhere to the roughened metal surface of the base plate;
    applying laser light to the roughened metal surface to desorb the substance to be analyzed from the roughened metal surface; and
    capturing the desorbed substance to perform mass spectrometry analysis.

2. The analysis method as claimed in claim 1,
    wherein the substance to be analyzed is ionized before applying the laser light to the roughened metal surface.

3. The analysis method as claimed in claim 1,
    wherein the substance to be analyzed is ionized by applying the laser light to the roughened metal surface.

4. An analysis method using a base plate comprising, on at least a portion of the surface thereof, a roughened metal surface capable of exciting local plasmon when exposed to laser light, the method comprising:
    contacting a sample with the roughened metal surface of the base plate;
    applying laser light to an area of the roughened metal surface having the sample contacting therewith to excite local plasmon;
    detecting the presence of a substance to be analyzed in the sample by utilizing the excitation of local plasmon;
    ionizing the substance;
    applying laser light to the area of the roughened metal surface having been exposed to the laser light for exciting local plasmon to desorb the ionized substance from the roughened metal surface; and
    capturing the desorbed ionized substance to perform mass spectrometry analysis.

5. An analysis apparatus using a base plate comprising, on at least a portion of the surface thereof, a roughened metal surface capable of exciting local plasmon when exposed to laser light, the apparatus comprising:
    a laser light applying means for applying laser light to the roughened metal surface of the base plate having a substance to be analyzed adhering thereto to desorb the substance from the roughened metal surface; and
    an analyzing means for capturing the substance desorbed from the roughened metal surface by the application of laser light and carrying out mass spectrometry analysis.

6. An analysis apparatus using a base plate comprising, on at least a portion of the surface thereof, a roughened metal surface capable of exciting local plasmon when exposed to laser light, the apparatus comprising:
    a laser light applying means for applying laser light to the roughened metal surface of the base plate having an ionized substance to be analyzed adhering thereto to desorb the substance from the roughened metal surface; and
    an analyzing means for capturing the substance desorbed from the roughened metal surface by the application of laser light and carrying out mass spectrometry analysis.

7. An analysis apparatus using a base plate comprising, on at least a portion of the surface thereof, a roughened metal surface capable of exciting local plasmon when exposed to laser light, the apparatus comprising:

a first laser light applying means for applying laser light to an area of the roughened metal surface having a sample contacting therewith to excite local plasmon;

a detecting means for detecting the presence of a substance to be analyzed in the sample by utilizing the excitation of local plasmon;

a second laser light applying means for applying laser light to the area of the roughened metal surface having been exposed to the laser light for exciting local plasmon to desorb the substance from the roughened metal surface; and an analyzing means for capturing the substance desorbed from the roughened metal surface by the application of laser light by the second laser light applying means and carrying out mass spectrometry analysis.

8. An analysis apparatus using a base plate comprising, on at least a portion of the surface thereof, a roughened metal surface capable of exciting local plasmon when exposed to laser light, the apparatus comprising:

a first laser light applying means for applying laser light to an area of the roughened metal surface having a sample contacting therewith to excite local plasmon;

a detecting means for detecting the presence of a substance to be analyzed in the sample by utilizing the excitation of local plasmon;

a second laser light applying means for applying laser light to the area of the roughened metal surface having been exposed to the laser light for exciting local plasmon to ionize the substance to be analyzed and to desorb ions of the substance to be analyzed from the roughened metal surface; and an analyzing means for capturing the ions desorbed from the roughened metal surface by the application of laser light by the second laser light applying means and carrying out mass spectrometry analysis.

\* \* \* \* \*